United States Patent [19]

Shah

[11] Patent Number: 5,059,207
[45] Date of Patent: Oct. 22, 1991

[54] SHAPED NEEDLES FOR SPECIALIZED SURGICAL PROCEDURES

[76] Inventor: Mrugesh K. Shah, 4314 Montevideo, Pasadena, Tex. 77504

[21] Appl. No.: 572,866

[22] Filed: Aug. 27, 1990

[51] Int. Cl.⁵ .............................................. A61B 17/00
[52] U.S. Cl. ..................................... 606/223; 606/224; 223/102
[58] Field of Search ............................. 606/223–226; 223/102

[56] References Cited

U.S. PATENT DOCUMENTS

| 67,545 | 8/1867 | Hodgins | 606/222 |
|---|---|---|---|
| 272,993 | 2/1883 | Vieman | 223/102 |
| 335,138 | 2/1886 | Merrill | 223/102 |
| 527,263 | 10/1894 | Blanchard | 606/223 |
| 1,377,359 | 5/1921 | Littlejohn | 606/223 |
| 1,449,068 | 3/1923 | Snyder | 223/102 |
| 1,751,796 | 3/1930 | Denner | 223/102 |
| 1,880,219 | 10/1932 | Sparke | 606/223 |
| 2,516,710 | 7/1950 | Mascolo | 606/223 |
| 2,811,157 | 10/1957 | Kurtz | 606/223 |
| 2,865,375 | 12/1958 | Banks | 606/223 |
| 2,865,376 | 12/1958 | Pellier | 606/222 |
| 3,038,475 | 6/1962 | Orcutt | 606/223 |
| 4,008,837 | 2/1977 | Hull | 223/102 |
| 4,345,601 | 8/1982 | Fukuda | 606/222 |
| 4,524,771 | 6/1985 | McGregor | 606/223 |
| 4,527,564 | 7/1985 | Eguchi | 606/223 |
| 4,699,142 | 10/1987 | Seal | 606/223 |
| 4,799,484 | 1/1989 | Smith | 606/223 |

Primary Examiner—Max Hindenburg
Assistant Examiner—Gary Jackson
Attorney, Agent, or Firm—Pravel, Gambrell, Hewitt, Kimball & Krieger

[57] ABSTRACT

Surgical needles having a "U" or "V" shaped body useful for suturing small, deep wounds typical of surgical procedures such as arthroscopy and laparoscopy are disclosed. Additionally, a method for suturing a deep incision using the "U" or "V" shaped body surgical needle is disclosed.

14 Claims, 3 Drawing Sheets 5,059,207

SHAPED NEEDLES FOR SPECIALIZED SURGICAL PROCEDURES

FIELD OF THE INVENTION

This invention relates generally to a shaped surgical needle and, more particularly, to a needle for use in specialized surgical procedures which require suturing of deep but narrow wounds, including procedures for arthroscopy and laparoscopy.

BACKGROUND OF THE INVENTION

Recent technological advances in the field of surgical needles have included improved materials, diameter, strength, and sharpness. However, few improvements, if any, have addressed needle shape.

Typical surgical needles vary widely in size, depending upon the surgical application, however most surgical needles are curved, or semicircular in shape. The broad, curved design is particularly useful in suturing of single layer wounds, for example, skin wounds.

Surgical needles are generally formed from wire into the desired curvature, for example, in the range of $\frac{1}{4}$ to $\frac{3}{8}$ circle, having a sharpened point or edge for cutting. Examples of prior art surgical needles include U.S. Pat. Nos. 2,811,157, 3,038,475, and 4,524,771.

The advent of new surgical procedures which utilize small, deep incisions through multiple layers of tissues, including arthroscopy and laparoscopy, have created a need for a new surgical needle shape. Use of the broadly curved surgical needles previously known in the art requires suturing each layer of a multiple tissue layer deep incision, requiring the placement of numerous sutures in the incision and requiring prolonged surgical time to complete the tissue repair. A needle design which would enable a surgeon to pass the needle with accuracy though multiple layers of tissue at one time, and at a controlled depth and width, would be of great utility in the suturing of small, deep surgical incisions.

SUMMARY OF THE INVENTION

Briefly, according to the invention, shaped surgical needles are provided that enable a surgeon to pass the needle with accuracy through multiple layers of tissue at one time, and at a controlled depth and width. The needles of the present invention are particularly useful for quickly and efficiently suturing deep wounds having a short width, for example, the incisions created in the tissues during the surgical procedures of arthroscopy and laparoscopy.

Advantageously, the surgical needles of the present invention provide a method for suturing a deep incision while reducing the number of sutures required and reducing the time required to make the tissue repair, by bringing together multiple layers of tissue with relatively few passes of the surgical needle, and in some procedures, with as few as one suture.

BRIEF DESCRIPTION OF THE DRAWINGS

The objects, advantages and features of the invention will become more apparent by reference to the drawings which are appended hereto and wherein like numerals indicate like parts and wherein an illustrative embodiment of the invention is shown, of which.

DETAILED DESCRIPTION OF THE INVENTION

Figure 1:
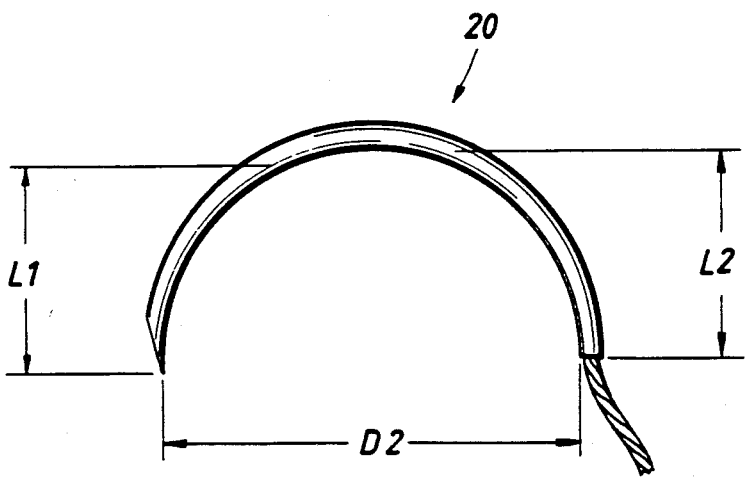
FIG. 1 is a side view of a conventional curved surgical needle of the prior art.

The surgical needles of the present invention are generally "U" or "V" shaped such as shown in FIGS. 2–10 as compared with the semicircular or curved shape of prior art needles, generally indicated at 20, shown in FIG. 1 and described in the above Background of the Invention Section.

Figure 2:
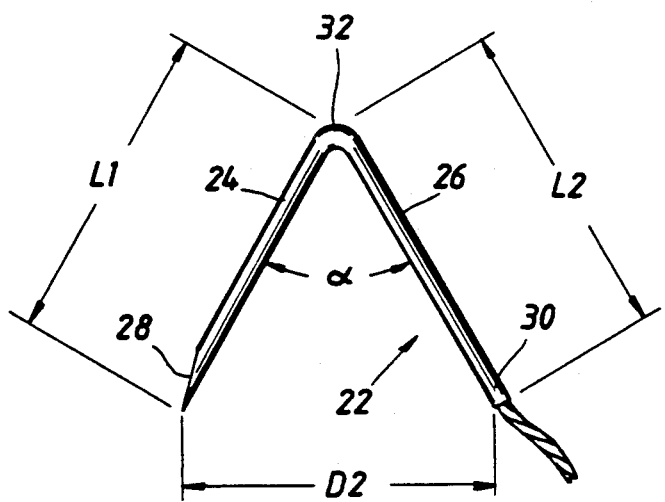
FIG. 2 is a side view of a "V" shaped needle of the present invention.

Referring to FIG. 2, the preferred embodiment of the "V" shaped needle includes a body, generally indicated at 22, having a centrally located bight or vertex 32 from which extends opposing arms 24,26. One arm 24 includes a distal pointed end 28. The end 30 of the opposite arm 26 is adapted to receive surgical suturing material. The two arms 24, 26 extend from the centrally located vertex 32 to create an internal angle $\alpha$ between them.

Figure 3:
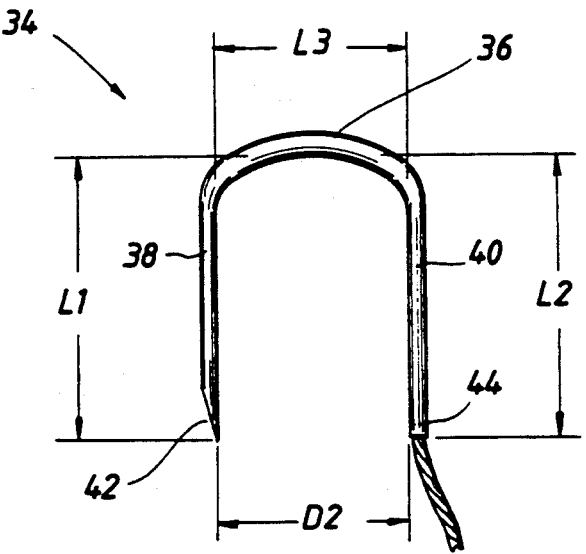
FIG. 3 is a side view of a "U" shaped needle of the present invention.
Figure 4:
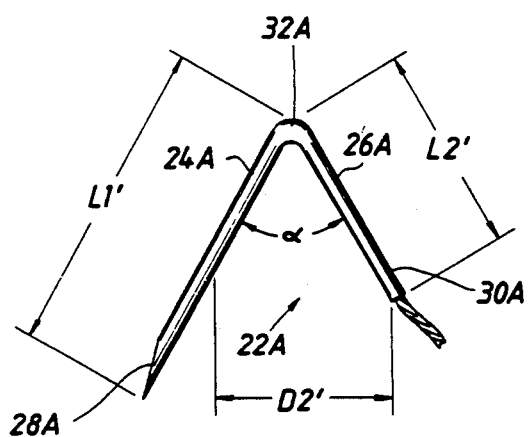
FIGS. 4 and 5 are side views of alternative embodiments of the "V" shaped needle of the present invention.
Figure 5:
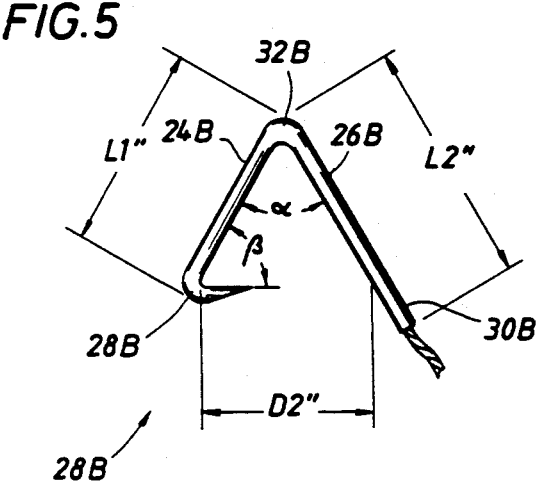

Referring now to FIG. 3, the preferred embodiment of the "U" shaped needle includes a body, generally indicated at 34, that includes a centrally located bight or semicircular arc 36 which is broader than that of the vertex 32 of the "V" shaped needles disclosed in FIGS. 2, 4 and 5. Arms 38, 40 include pointed end 42 and end 44 adapted to receive surgical suturing material, respectively.

Turning now to FIGS. 2 and 3, the length L1, L2 of the arms of the "U" and "V" shaped needles is in the range of 0.5 to 10.0 cm in total length, and preferably in the range of 1.0 to 5.0 cm. The gap D2 of the needles shown in FIGS. 2 and 3 between the distal ends of the arms is in the range of 0.5 cm to 10.0 cm, preferably 0.5 to 5.0 cm. The length of the gap D2 is less than or equal to the length L1, L2 of the arms, with a ratio of the gap D2 to each length L1, L2 in the range of 0.1:1.0 to 1.0:1.0. Preferably, this ratio is in the range of 0.5 to 1.0.

An alternative embodiment of the "V" shaped needle is shown in FIG. 4, including a body, generally indicated as 22A, and having arms 24A, 26A which are unequal in length L1', L2'; L1' being greater in length than L2', and D2' being less than or equal to the length of either L1' or L2'. D2' is taken at the end of the arm with the shortest length, in the case L2'.

Figure 7:
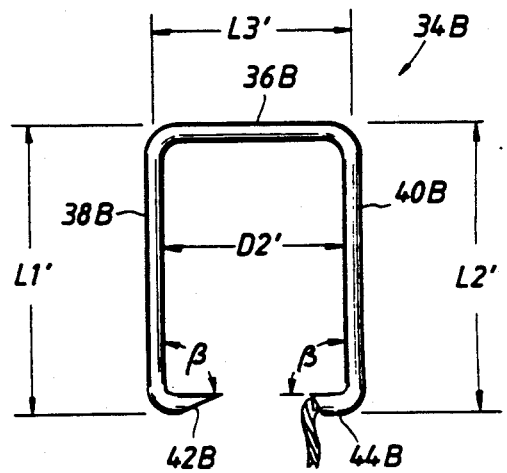

An alternative embodiment of the "V" shaped needle is shown in FIG. 5. L1" is less in length than L2" but D2" is less than either L1" or L2". As shown in FIGS. 5 and 7, the distal ends may be bent toward the gap D2 at an angle $\beta$. The angle $\beta$ may be in the range of approximately 25° to 90°, and preferably is approximately 45° for a "V" shaped needle, such as shown in FIG. 5 and preferably is approximately 90° for a "U" shaped needle such as shown in FIG. 7.

The preferred size and shape of the needle will vary with the type of wound to be sutured, its depth, width, and tissue type, and will also vary with the size of the patient and the amount of fat at the site of the wound. Preferably, the length L1, L2 of the arms 24, 26, 38, 40 is greater than or equal to the gap distance D2. In the suturing of deep wounds in a tissue containing large amounts of fat, a "U" or "V" shaped needle having a gap distance D2 of less than the length L1, L2 of the arms is preferred.

Preferably, the length L1, L2 of the arms 24, 26 is in the range of approximately 0.5 to 10 cm and the vertex 32 of a "V" shaped needle preferably has an angle $\alpha$ in the range of 10° to 45°. For example, the preferred embodiment "V" shaped needle of approximately 4–6 cm in arm length L1, L2 and having a bight or vertex 32 with an angle $\alpha$ of approximately 30°–45° is useful in the suturing of a typical arthroscopy incision of approximately 3 to 5 cm in depth and approximately 1 cm in width, as shown generally in FIG. 9.

Figure 6:
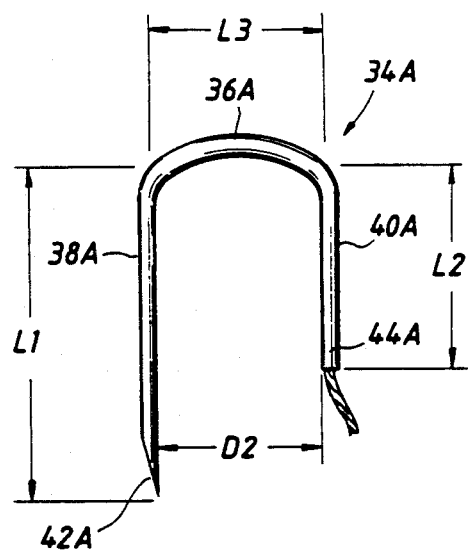
FIGS. 6–8 are side views of alternative embodiments of the "U" shaped needle of the present invention.
Figure 8:
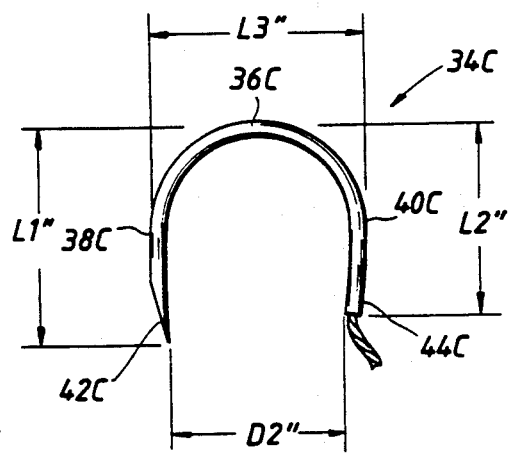

Preferably, the "U" shaped needle has a central semicircular arc 36 which has a length L3 equal to or less than either length L1, L2 of the arms 38, 40 on D2 is less than or equal to L1, L2 or L3, as shown in FIGS. 6–8. For example, the "U" shaped needle as shown in FIG. 7 having arms 38B, 40B of approximately 2.5 cm length, and a central semicircular arc 36B of approximately 2.5 cm length, and having distal ends 42B, 44B which are bent toward the gap D2 with an approximate angle of 90°, is useful in the suturing of abdominal incisions below the level of the skin, as shown in use in FIG. 10.

The body of the needle of the present invention may be circular in cross section, or may have an alternative cross-sectional shape. Examples of alternative cross-sectional shapes include those disclosed in U.S. Pat. No. 4,524,771, which U.S. patent is hereby incorporated herein for all purposes.

The pointed end of the needle may also be circular in cross section, or may be formed of an alternative shape design, examples of which are disclosed in U.S. Pat. Nos. 2,811,157 and 4,524,771, which U.S. patents are hereby incorporated herein for all purposes.

Opposite the pointed end, the distal end is adapted to receive a suture material. Such adaptation may be a drilled, hollow end of the needle, an eye, a clip, or other adaption for receiving a suture material. The suture material may be any of the known suture materials known in the art, including nylon and absorbable suture materials.

The needles of the present invention may be made from any of the materials known to be useful for surgical needles, including stainless steel wire having a diameter of from 0.003 cm to 0.020 cm. The needles may be manufactured to conform with the above described characteristics by any of the techniques well known in the art of needle manufacturing. One method for manufacturing the needles is to first straighten a length of wire from a coil. The diameter of the wire may be 4 mil, 6 mil, or other diameter as desired. The straightened wire may be cut to the desired length.

One end of the wire is ground by standard techniques to provide a tapered configuration and generally a pointed end. The unground or blunt end is treated to provide a means for attaching a suture material to that end. This treatment may comprise drilling the end of the needle to provide a hole in the end and is well known. The wire is then bent to conform to the desired shape.

A needle of the present invention may be used to suture deep wounds by passing the needle through multiple layers of tissue at one time, and bringing the multiple layers of tissue to closure with fewer sutures than required by prior art needles. For example, as shown generally in FIG. 9, the needle of the present invention may pass through layers of tissue including epidermis 42, dermis 44, superficial fascia and fat 46, deep fascia 48, and muscle 52 in a single suture.

Figure 9:
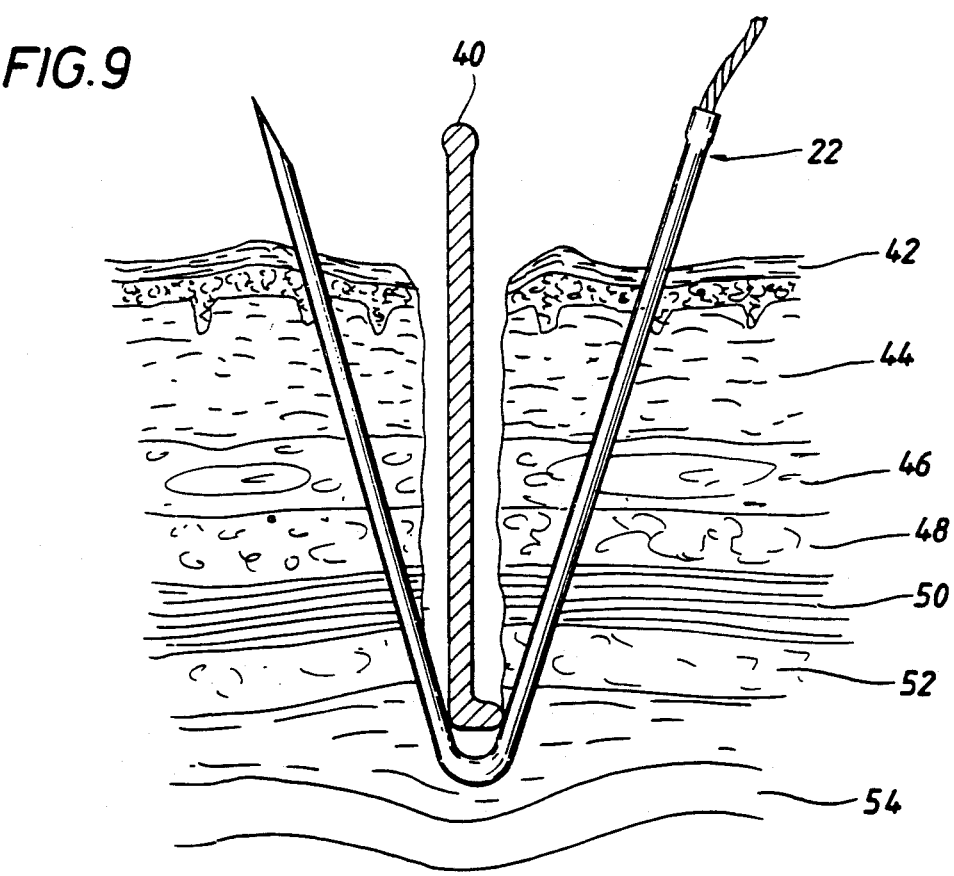
FIG. 9 is an elevational cross-section view of the penetration of multiple layers of tissue by a "V" shaped needle.
Figure 10:
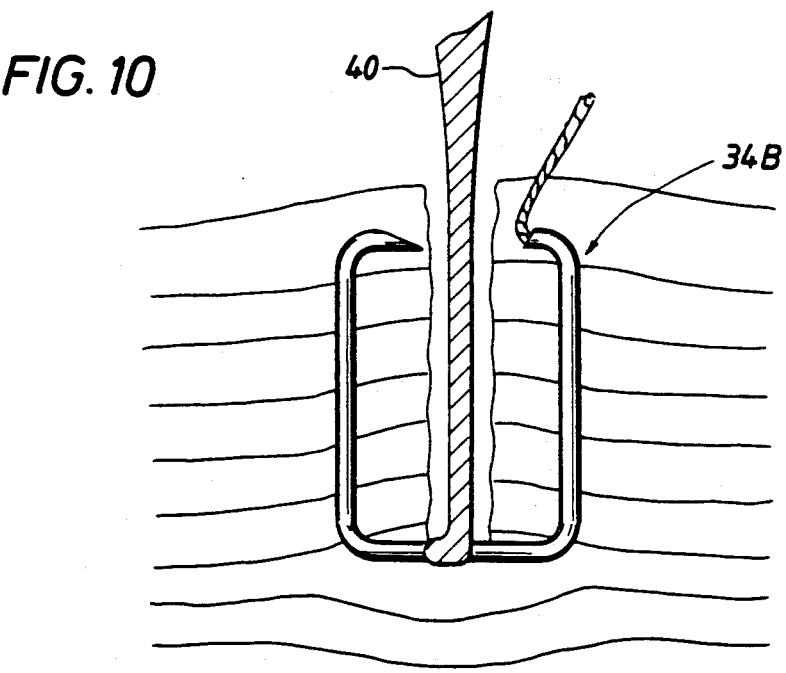
FIG. 10 is an elevational cross-section view similar to FIG. 9 though showing the penetration of multiple layers of tissue by a "U" shaped needle of the structure of FIG. 7.

In using a needle of the present invention, the needle is gripped with a typical needle holder, such as a hemostat, near the distal end of the second arm. A tool 40 as shown in FIGS. 9 and 10, such as a blunt probe, is inserted into the puncture wound and used to depress the organs 54 and tissue underlying the area to be sutured. The inserted tool 40 may also serve as a guide during the suturing process, guiding the inserted needle to a predetermined depth. The pointed distal end of the needle is directed into the tissue to be penetrated. The inward position is maintained until the desired tissue depth is reached, preferably, facilitated by the inserted tool 40. The needle is then abruptly turned, preferably passing under the inserted tool 40, such that the pointed distal end assumes a trajectory in the outward direction, returning the pointed distal end to the surface of the tissue, exiting the tissue on the opposite side of the wound and thereby establishing the bite the suture has taken. By this method, closure of a deep puncture-type wound at multiple tissue layers is accomplished using one or more sutures.

In general, the gap distance D2 of the needle used will determine the bite of the suture. Preferably, for the needles of the present invention, this distance is in the range of approximately 0.5 to 10 cm, more preferably in the range of approximately 1.0 to 5.0 cm.

The foregoing disclosure and description of the invention are illustrative and explanatory thereof, and various changes in the size, shape and materials, as well as in the details of the illustrated construction may be made without departing from the spirit of the invention.

What is claimed is:

1. A shaped surgical needle adapted for suturing a wound, the needle comprising:
   a body:
   a bight in the body;
   a first arm and a second arm extending from the bight, each arm having a predetermined length and an end opposite the bight, said first arm having a length no greater than the length of said second arm;
   a gap distance between the end of said first arm and a point on said second arm located a distance from the bight corresponding to the length of said first arm, said gap distance being no greater than the length of said first arm;
   a sharpened point on the end of one of said arms; and
   a device at the end of the other of said arms for securing a suturing material.

2. The needle of claim 1 wherein the bight formed between the first and second arm is in the range of 10° to 45°.

3. The needle of claim 1 wherein the first and second arms are of equal length.

4. The needle of claim 1 wherein the first arm has a length longer than the second arm.

5. The needle of claim 1 wherein the length of said arms is in the range of 0.5 to 10.0 cm.

6. The needle of claim 1 wherein a gap distance between the end of said first arm and the end of said second arm is in the range of 0.5 cm to 10 cm.

7. A method for suturing a wound comprising the steps of:
   inserting a shaped needle having a pointed first end and a second end into tissue adjacent to the wound to a predetermined depth, said shaped needle includes a body having a bight, and having a first and second arm extending from said bight, each arm having a predetermined length and an end opposite the bight, said first arm having a length no greater than the length of said second arm;
   a gap distance between the end of said first arm and a point on said second arm located a distance from the bight corresponding to the length of said first arm, said gap distance being no greater than the length of said first arm;
   moving the inserted needle such that the pointed end of the needle assumes a path to exit the tissue adjacent to the wound on the opposite side of the wound from the initial point of intersection; and
   removing the needle from the tissue such that the suturing material remains in the tissue.

8. The method of claim 7, further comprising the step of:
   inserting a tool into the wound to depress underlying tissue.

9. The method of claim 8 wherein the tool facilitates locating of the predetermined depth.

10. The method of claim 7, wherein said inserting step is inserting a "V" shaped needle having a bight angle in the range of 10° to 45° formed between said first and second arms.

11. The method of claim 7, wherein said inserting step is inserting a "U" shaped needle having a semicircular arc.

12. The method of claim 7, wherein the distance between said point of insertion and said exit from the tissue is in the range of 0.5 to 10.0 cm.

13. The method of claim 7, wherein said insertion step is through multiple layers of tissue.

14. The method of claim 7, wherein said inserting, moving, and removing steps are repeated to effect closure of said wound.

* * * * *